(12) United States Patent
Calhoun et al.

(10) Patent No.: US 6,956,023 B1
(45) Date of Patent: Oct. 18, 2005

(54) MATERIALS AND METHODS FOR PROVIDING NUTRITION TO NEONATES

(75) Inventors: Darlene V. Calhoun, Bradenton, FL (US); Robert D. Christensen, St. Petersburg, FL (US)

(73) Assignee: University of Florida, Gainesville, FL (US)

( * ) Notice: Subject to any disclaimer, the term of this patent is extended or adjusted under 35 U.S.C. 154(b) by 58 days.

(21) Appl. No.: 10/125,967

(22) Filed: Apr. 19, 2002

Related U.S. Application Data

(60) Provisional application No. 60/284,809, filed on Apr. 19, 2001.

(51) Int. Cl.$^7$ .................. A61K 38/18; A61K 45/00; C07K 14/535; C07K 14/505
(52) U.S. Cl. .................. 514/2; 530/350; 530/395; 530/399; 424/85.1
(58) Field of Search .................. 514/2; 530/350, 530/395, 399

(56) References Cited

U.S. PATENT DOCUMENTS

| | | | |
|---|---|---|---|
| 4,377,513 A | 3/1983 | Sugimoto et al. | |
| 4,703,008 A | 10/1987 | Lin | |
| 4,810,643 A | 3/1989 | Souza | |
| 4,835,260 A | 5/1989 | Shoemaker | |
| 5,206,219 A | 4/1993 | Desai | |
| 5,399,551 A | 3/1995 | Ise et al. | |
| 5,540,945 A | 7/1996 | Ikushima | |
| 5,574,136 A | 11/1996 | Nagata et al. | |
| 5,580,755 A | 12/1996 | Souza | |
| 5,597,562 A | 1/1997 | Nomura et al. | |
| 5,621,080 A | 4/1997 | Lin | |
| 5,681,720 A | 10/1997 | Kuga et al. | |
| 5,955,422 A | 9/1999 | Lin | |
| 5,965,121 A | 10/1999 | Leone-Bay et al. | |
| 6,096,728 A * | 8/2000 | Collins et al. | ............... 514/2 |
| 6,376,218 B1 | 4/2002 | Hsu et al. | |

FOREIGN PATENT DOCUMENTS

GB 2 283 912 A * 5/1995

OTHER PUBLICATIONS

Todd et al. Temporary banding of the gastroesophageal juncture in a very small neonate with esophageal atresia and tracheoesophagea fistula. Abstract, Minnesota Medicine 73 (7) 30-2 (1990).*
Ledbetter et al. Necrotizing enterocolitis and hematopoietic cytokines, Clinics in Perinatology vol. 27/3:697-716 (Sep. 2000).*
Bernt, K.M. et al. "Human milk as a carrier of biochemical messages" *Acta Paediatr Suppl.*, 1999, 430:27-41.
Carmichael, R.D. et al. "The Effects of Maternal Phlebotomy and Orally-Administered Erythropoietin (Ep) on Erythropoiesis in the Sucking Rat" *Biol. Neonate*, 1978, 33:119-131.
Koldovsky, O. "Search for role of Milk-Borne Biologically Active Peptides for the Suckling" *J. Nutr.*, 1989, 119:1543-1551.
Rodriguez-Palmero, M. et al. "Nutritional and Biochemical Properties of Human Milk: II" *Clinics in Perinatology*, Jun. 1999, 26(2):355-359.
Ames, M., "Gastric acidity in the first ten days of life of the prematurely born baby" *Am J. Dis. Child*, 1966, 100:252-256.
Benzie, R.J. et al., "Composition of the amniotic fluid and maternal serum in pregnancy" *Am J Obstet Gynecol*, 1974, 119:798-810.
Berseth, C.L. et al., "Birth asphyxia alters neonatal intestinal motility in term neonates" *Pediatrics*, 1992, 90:669-673.
Bonsnes, R., "Composition of amniotic fluid" *Clin Obstet Gynecol*, 1966, 9:440-448.
Britton, J.R. et al., "Enteral administration of recombinant erythropoietin to preterm infants" *J. Perinatol.*, 1995, 15(4):281-283.
Britton, J.R. and Koldovsky, O., "Development of luminal protein digestion: Implications for biologically active dietary polypeptides" *J. Pediatr. Gastroenterol. Nutr.*, 1989, 9(2):144-162.
Buescher, U. et al., "Erythropoietin in amniotic fluid as a marker of chronic fetal hypoxia" *Int J Gynaecol Obstet*, 1998, 60:257-263.
Calhoun, D. et al., "Distribution of granulocyte colony-stimulating factor (G-CSF)-receptor mRNA and protein in the human fetus" *Pediatr. Res.*, 1999, 43:333-338.
Calhoun, D. et al., "Concentrations of granulocyte colony-stimulating factor in human milk after in vitro simulations of digestion" *Pediatr. Res.*, , 1999, 46:767-771.
Calhoun, D. et al., "Stability of filgrastim and epoetin alfa in a system designed for enteral administration in neonates" *The Annals of Pharmacotherapy*, 2000, 34:1257-1261.
Calhoun, D. et al., "Granulocyte colony-stimulating factor is present in human milk and its receptor is present in human fetal intestine" *Pediatrics*, Jan. 2000, 105(1):E7.

(Continued)

Primary Examiner—Elizabeth Kemmerer
Assistant Examiner—Regina M. DeBerry
(74) Attorney, Agent, or Firm—Saliwanchik, Lloyd & Saliwanchik

(57) ABSTRACT

The subject invention provides methods for reducing or preventing villous atrophy and feeding intolerance in infants, particularly low birth weight and/or preterm infants, by enterally administering granulocyte-colony stimulating factor (G-CSF), erythropoietin (Epo), or both G-CSF and Epo. The subject invention also provides compositions that comprise G-CSF and/or Epo that may be administered to infants in need thereof. In one embodiment, the composition of the subject invention comprises recombinant G-CSF, recombinant Epo, and one or more electrolyte additives. In a specific embodiment, the electrolyte additive is selected from the group consisting of sodium chloride, sodium acetate, and potassium chloride.

48 Claims, 4 Drawing Sheets

OTHER PUBLICATIONS

Calhoun, D. et al., "Granulocyte colony-stimulating factor in preterm and term pregnancy, parturition, and intra-amniotic infection" *Obstet Gynecol*, 2001, 97:229-234.

Clapp, J. et al., "The effect of regular maternal exercise on erythropoietin in cord blood and amniotic fluid" *Am. J. Obstet. Gynecol.*, 1995, 172(5):1445-1451.

Lind, T., et al., "Composition of amniotic fluid and maternal blood through pregnancy" *J. Obstet Gynaecol*, 1971, 78: 505-512.

McCracken, S. et al., "Expression of granulocyte-colony stimulating factor and its receptor is regulated during the development of the human placenta" *J. Endocrinol.*, 1996, 149:249-258.

Mulvihill, S., et al., "Trophic effect of amniotic fluid on fetal gastrointestinal development" *J. Surg. Res.*, 1986, 40:291-296.

Ohls, R. and Christensen R., "Stability of human recombinant epoetin alfa in commonly used neonatal intravenous solutions" *Ann. Pharmacother*, 1996, 30:466-468.

Schanler, R. et al., "Feeding strategies for premature infants: Randomized trial of gastrointestinal priming and tube-feeding method" *Pediatrics*, 1999, 103(2):434-439.

Scholz, T. and McGuinness, G., "Localized intestinal perforation following intravenous indomethacin for patent ductus arteriosus" *J. Pediatr. Gastroenterol Nutr.*, 1988, 7:773-775.

Sinha, J., "The volume and compostion of amniotic fluid in early pregnancy" *Obstet. Gynaecol.*, 1970, 77:211-214.

Tada, M. et al., "Analysis of cytokine receptor messenger RNA expression in human glioblastoma cells and normal astrocytes by reverse-transcription" *J. Neurosurg.*,1994, 80: 1063-1073.

Trahair, J. and Harding, R., "Restitution of swallowing in the fetal sheep restores intestinal growth after midgestation esophageal obstruction", *J. Pediatr. Gastroenterol. Nutr.*, 1995, 20:156-161.

Cothran, D. et al., "Alteration of normal gastric flora in neonates receiving ranitidine" *J. Perinatol*, 1997, 17(5):383-388.

Emery, A. et al., "Antenatal diagnosis and aminoacid composition of amniotic fluid" *Lancet*, 1970, 760:1307-1308.

Gersting, J. et al., "Evaluation of the enteral administration of recombinant human granulocyte colony-stimulating factor (rhG-CSF) to mouse pups with an intact G-CSF-Receptor (G-CSF-R) gene (WT) and pups deficient for the G-CSF-R gene (KO)" *Pediatr. Res.*, 2000, 47(4), p. 287A, abstract No. 1696.

Giacoia, G. et al., "Indomethacin and recurrent ileal perforations in a preterm infant" *J. Perinatol*, 1993, 13:297-299.

Gilmore, W. et al., "Human milk contains granulocyte colony stimulating factor" *Eur. J. Clin. Nutr.*, 1994, 48:222-224.

Juul, S. et al., "Tissue distribution of erythropoietin and erythrpoietin receptor in the developing human fetus" *Early Hum. Dev.*, 1998, 52:235-249.

Juul, S. et al., "Immunohistochmemical localization of erythropoietin and its receptor in the developing human brain" *Pediatr. Dev. Pathol.*, 1999, 2:148-158.

Juul, S., et al., "Why is erythropoietin present in human milk? Studies of erythropoietin receptors on enterocytes of human and rat neonates" *Pediatr. Res.*, 1999, 46(3):263-268.

Juul, S. et al., "The effects of enteral vs parenteral recombinant erythropoietin (rEpo) on bowel growth" *Pediatr. Res.*, 2000, 47(4), p. 165A, abstract No. 971.

Juul, S. et al., "The origin, fate, and function of erythropoietin in human milk" *Pediatr. Res.*, 2000, 47(4), p. 289A, abstract No. 1707.

Kelly, E. et al., "Gastric acid secretion in preterm infants" *Early Hum. Dev.*, 1993, 35:215-220.

Kling, P. et al., "Human milk as a potential enteral source of erythropoietin" *Pediatr. Res.*, 1998, 43,(2):216-221.

Ledbetter, D.J. et al., "Erythropoietin and the incidence of necrotizing enterocolitis in infants with vary low birth weight" *J. Pediatr. Surg.*, 2000, 35(2):178-182.

Berseth, C. "Minimal enteral feedings" *Clinics in Perinatology*, Mar. 1995, 22(1):195-205.

Calhoun, D. et al. "Granulocyte colony-stimulating factor in preterm and term pregnancy, parturition, and intra-amniotic infection" *Obstet. Gynecol.*, Feb. 2001, 97(2):229-234.

Karnak, I. et al. "Esophageal ligation: Effects on the developmental of fetal organic systems" *Eur. J. Pediatr. Surg.*, 1996, 6:328-333.

Klurfeld, D. "Nutritional regulation of gastrointestinal growth" *Frontiers in Bioscience*, Jan. 1, 1999, 4:d9-21.

Saito, M. et al. "Origin of macrophage colony-stimulating factor (M-CSF) and granulocyte colony-stimulating factor (G-CSF) in amniotic fluid" *Asia-Oceania J. Obstet. Gynaecol.*, 1992, 18:355-361.

Wallace, J. M. et al. "Cytokines in human breast milk" *Br. J. Biomedical Sci.*, 1997, 54:85-87.

Bernstein, H.M. et al. "Administration of recombinant granulocyte colony-stimulating factor to neonates with septicemia: A meta-analysis" *J. Pediatr.*, 2001, 138(6):917-920.

Calhoun, D.A. and Christensen, R.D. "A randomized pilot trial of administration of granulocyte colony-stimulating factor to women before preterm delivery" *Am J. Obstet. Gynecol.*, 1998, 179:766-771.

Calhoun, D.A. and Christensen, R.D. "Recent advances in the pathogenesis and treatment of nonimmune neutropenias in the neonate" *Curr. Opin. Hematol.*, 1998, 5(1):37-41.

Calhoun, D.A. et al., "Consistent approaches to procedures and practices in neonatal hematology" *Clin. Perinatol.*, 2000, 27(3):733-753.

Calhoun, D.A. and Christensen, R.D. "Human developmental biology of granulocyte colony-stimulating factor" *Clin. Perintol.*, 2000, 27(3):559-576.

Calhoun, D.A. et al. "Granulocyte-macrophage colony-stimulating factor and interleukin-5 concentrations in premature neonates with eosinophilia" *J. Perinatol.*, 2000, 20(3):166-171.

Calhoun, D.A. et al. "Granulocyte colony-stimulating factor serum and urine concentrations in neutropenic neonates before and after intravenous administration of recombinant granulocyte colony-stimulating factor" *Pediatrics*, 2000, 105(2):392-397.

Calhoun, D.A. "Enteral administration of hematopoietic growth factors in the neonatal intensive care unit" *Acta Paediatr. Suppl.*, 2002, 91(438):43-53.

Calhoun, D.A. et al. "G-CSF and Epo stability in amniotic fluid during simulated in vitro digestion conditions" *J. Pharm. Tech.*, 2002, 18:310-315.

Calhoun, D.A. et al. "Recombinant granulocyte colony-stimulating factor administered enterally to neonates is not absorbed" *Pediatrics*, 2003, 112:421-423.

Condino, A. et al. "Abnormal intestinal histology I neonates with congenital anomalies of the gastrointestinal tract" *Early Human Development*, Epub ahead of print, Nov. 25, 2003.

Gersting, J.A. et al. "The Effects of Enterally Administering Granulocyte Colony Stimulating Factor to Suckling Mice" *Pediatric Research*, in press 2003.

Gersting, J.A. et al. "Bioavailability of Granulocyte Colony-Stimulating Factor Administered Enterally to Suckling Mice" *Pharmacological Res.*, 2003, 48:643-647.

Lima, V. et al., "Enteral administration of a sterile isotonic solution containing recombinant growth factors to neonates recovering from necrotizing enterocolitis: A Phase I dose-escalation trial" *J. Perinatology*, 2003, 23:200-204.

Papoff, P. et al. "Granulocyte colony-stimulating factor, granulocyte macrophage colony-stimulating factor and neutrophils in the bronchoalveola lavage fluid of premature infants with respiratory distress syndrome" *Biol. Neonate.*, 2001, 80(2):133-141.

Sullivan, S.E. et al. "Circulating concentrations of chemokines in cord blood, neonates, and adults" *Pediatr. Res.*, May 2002, 51(5):653-657.

Sullivan, S.E. et al. "Tolerance of simulated amniotic fluid in premature neonates" *Ann. Pharmacother.*, , 2002, 36(10): 1518-1524.

* cited by examiner

Percent of rG-CSF in Composition After Simulated Digestions

Percent of G-CSF in Natural Amniotic Fluid After Simulated Digestions

Percent of G-CSF in Natural Amniotic Fluid with Additional rG-CSF Simulated Digestions Percent of rG-CSF in Composition After Simulated Digestions ▨ pH 3.2 glycine
☐ pH 4.5 maleate
▨ pH 5.8 maleate Percent of Epo in Natural Amniotic Fluid After Simulated Digestions Percent of Epo in Natural Amniotic Fluid with Additional rEpo After Simulated Digestions

MATERIALS AND METHODS FOR PROVIDING NUTRITION TO NEONATES

CROSS-REFERENCE TO RELATED APPLICATION(S)

This application claims the benefit of provisional patent application Ser. No. 60/284,809, filed Apr. 19, 2001.

The subject invention was made with government support under a research project supported by the National Institute of Child Health Grant No. HD01180. The government may have certain rights in this invention.

BACKGROUND OF THE INVENTION

Granulocyte-colony stimulating factor (G-CSF) and erythropoietin (Epo) have important nonhematopoietic roles in human developmental biology (Calhoun et al. [1999] (A) *Pediatr Res* 43:333–338; Tada et al. [1994] *J. Neurosurg* 80:1063–1073; McCracken et al. [1996] *J Endocrinol* 149: 249–258; Ledbetter, D. J. et al. [2000] *J. Pediatr Surg* 35:178–182; Juul et al. [1998] *Early Hum Dev.* 52:235–249; Juul et al. [1999] (A) *Pediatr Dev. Pathol* 2:148–158). Among these roles, both G-CSF and Epo are trophic factors for the developing intestine (Juul et al. [1999] (B) *Pediatr Res* 46:263–8; and Gersting et al. [2000] *Pediatr Res* 47:287A).

The lumenal surface of the fetal and neonatal intestine is constantly exposed to G-CSF and Epo, since both are present in high concentrations in ingested fluids, including amniotic fluid, (Calhoun et al [1998] *J Soc Gynecol Invest.* 5:176A; Saito et al. [1992] *Asia Oceania J Obstet Gynaecol* 18:355–61; Clapp et al. [1995] *Am J Obstet Gynecol* 172 1445–51; Buescher et al. [1998] *Int J Gynaecol Obstet* 60: 257–263) colostrum, (Calhoun et al. [2000] *Pediatrics* 105: e7; Kling et al. [1998] *Pediatr Res* 43: 216–21) and milk (Calhoun et al. [2000] *Pediatrics* 105:e7; Kling et al. [1998] *Pediatr Res* 43: 216–21; Wallace et al. [1997] *Br J Biomed Sci* 54:87; Gilmore et al. [1994] *Eur J Clin Nutr* 48:222–4). Moreover, ingested G-CSF and Epo are highly protected from digestion in the neonatal intestine (Kling et al. [1998] supra; Wallace et al [1997] supra; Gilmore et al. [1994] supra; Calhoun et al. [1999] (B) *Pediatr Res* 46:767–71), and specific receptors for G-CSF and for EPO are expressed on the surface of fetal villous enterocytes (Calhoun et al. [1999] (A) supra; Juul et al. [1998] supra; Calhoun et al. [2000] supra). Animal studies and in vitro culture models indicate that binding of G-CSF and Epo to their cognate receptors on enterocytes results in trophic actions on villous height and bowel length (Juul et al. [1999] (B) supra; Gersting et al. [2000] supra; Juul et al. [2000] (A) *Pediatr Res* 47:289 A; and Juul et al. [2000] (B) *Pediatr Res* 47:165 A).

With preterm birth, the ingestion of amniotic fluid containing G-CSF, Epo, and other intestinal trophic factors ceases abruptly. It is often necessary in neonatology to withhold enteral feedings from extremely low birth weight (<1000 g) or preterm infants for days to weeks, relying exclusively, for that period of time, on parenteral nutrition (Giacoia et al. [1993] *J Perinatol* 13:297–9; Scholz et al. [1988] *J Pediatr Gastroenterol Nutr* 7:773–5; Schanler et al. [1999] *Pediatrics* 103:434–9; and Berseth et al. [1999] *Front Biosci* 4: d299–302). However, in such patients, villous atrophy occurs, and this likely predisposes them to feeding intolerance and necrotizing enterocolitis once feedings are instituted (Ledbetter et al. [2000] supra; Berseth et al. [1992] *Pediatrics* 90:669–73; Klurfeld [1999] *Front Biosci*4:D299–302; Mulvihill et al. [1 *J Surg Res* 40:291–6; Trahair [1995] *J Pediatr Gastroenterol Nutr* 20:156–61; and Karnak et al. [1996] *Eur J Pediatr Surg* 6:328–33).

Because the abrupt cessation in trophic factors swallowed in utero and the delay in receiving quantities of these growth factors in human milk likely result in villous atrophy and predispose preterm infants to feeding intolerance, it would be advantageous to provide low birth weight and/or preterm infants with critical intestinal trophic factors comparable to those they would have ingested from amniotic fluid had they remained in utero.

BRIEF SUMMARY OF THE INVENTION

The subject invention provides methods and compositions that promote or facilitate nutritional intake in low birth weight and/or preterm infants. Specifically, the subject invention provides methods for reducing or preventing villous atrophy and feeding intolerance in low birth weight and/or preterm infants by enterally administering granulocyte-colony stimulating factor (G-CSF), erythropoietin (Epo), or both G-CSF and Epo. In one aspect of the subject invention, recombinant G-CSF (rG-CSF, known generically as filgrastim) and/or recombinant Epo (rEpo, known generically as epoetin alfa) are administered. In a preferred embodiment of the subject invention, both G-CSF and Epo are administered. In a further preferred embodiment, G-CSF and Epo are administered to the neonate in concentrations comparable to those they would have ingested from amniotic fluid had they remained in utero. In addition to reducing or preventing villous atrophy and feeding intolerance, the methods of the subject invention decrease the incidence of necrotizing enterocolitis in the low birth weight and/or preterm infant.

The subject invention also provides compositions that comprise G-CSF and/or Epo that may be administered to low birth weight and/or preterm infants in need thereof. In one embodiment, the composition of the subject invention comprises rG-CSF, rEpo, and one or more electrolyte additives. In a specific embodiment, the electrolyte additives are selected from the group consisting of sodium chloride, sodium acetate, and potassium chloride.

The compositions of the subject invention can be administered to a low birth weight and/or preterm infant enterally. Preferably, the compositions are administered orogastrically and/or nasogastrically.

While the methods and compositions of the subject invention are particularly useful for facilitating nutritional intake in low birth weight and/or preterm infants, the methods and compositions of the subject invention are also directed to infants suffering from any condition in which they are placed in the medical category of NPO (nothing per orum), receiving nothing by mouth. These infants often develop villous atrophy within 24 hours of not eating and may or may not be preterm and/or low birth weight.

Filgrastim concentrations were determined in aliquots of fresh solution before priming of a polyvinyl chloride feeding tube, during priming with 3 mL of solution, and after priming with 3 mL.

Figure 3:
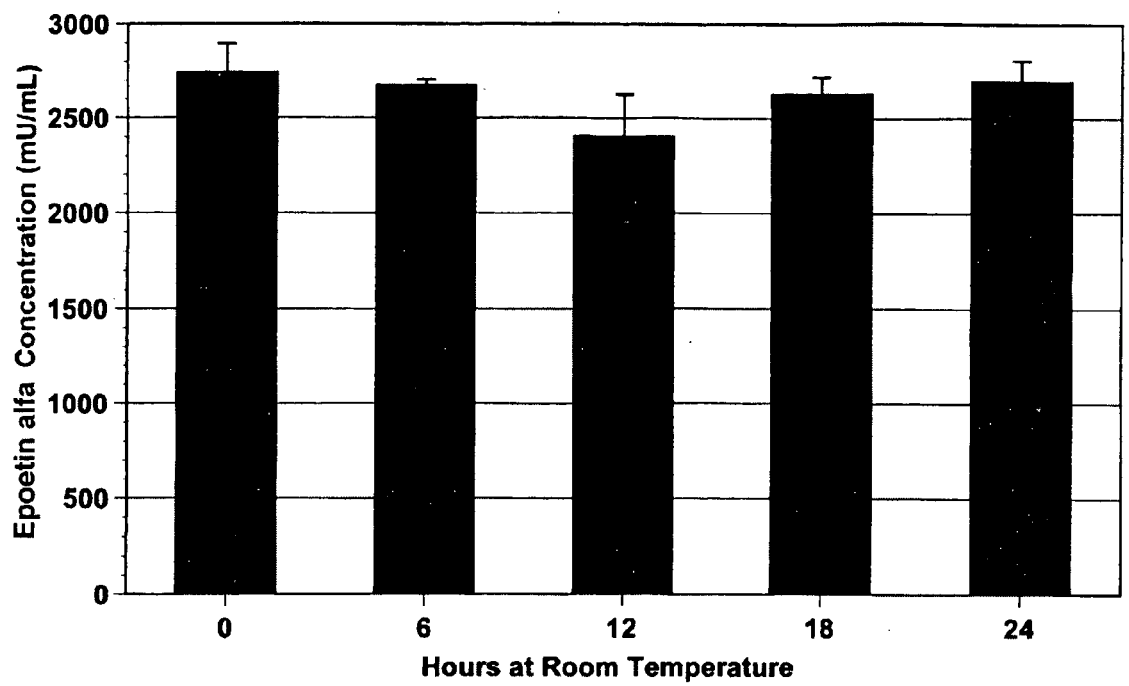

FIG. 3 shows epoetin alfa concentrations (mean+/−SEM) in a composition of the subject invention. The concentration of epoetin alfa was measured in aliquots of solution stored at room temperature for up to 24 hours. At specific intervals (6, 12, 18, or 24 hours) aliquots were frozen at −80° C. until analysis. Each time point represents the average concentration of five solutions (p=0.001).

Figure 4:
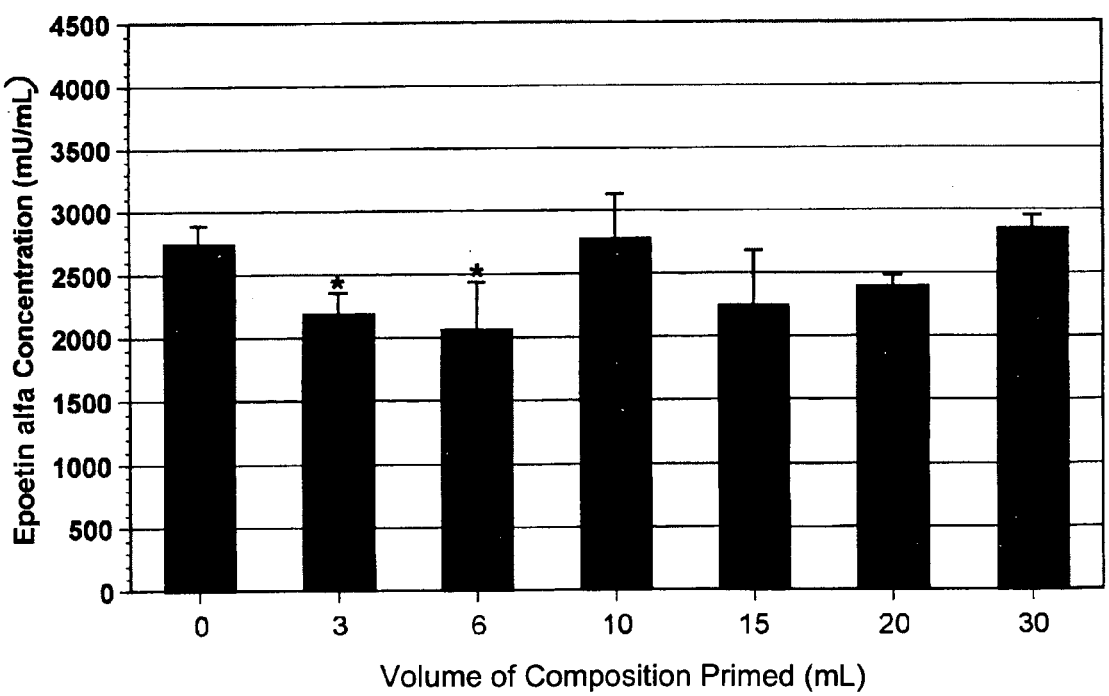

FIG. 4 shows epoetin alfa concentrations (mean+/−SEM) before, during, and after priming of the feeding tube. Epoetin alfa concentrations were determined in aliquots of fresh solution before priming of a polyvinyl chloride feeding tube, during priming with 3 mL of solution, and after priming with 10 mL (p=0.001).

Figure 5A:
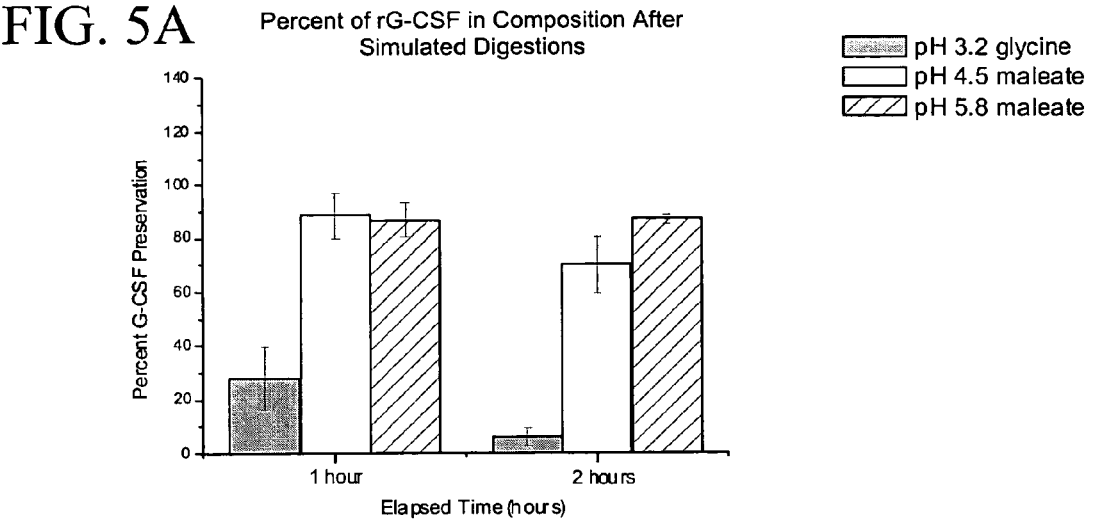
Figure 5B:
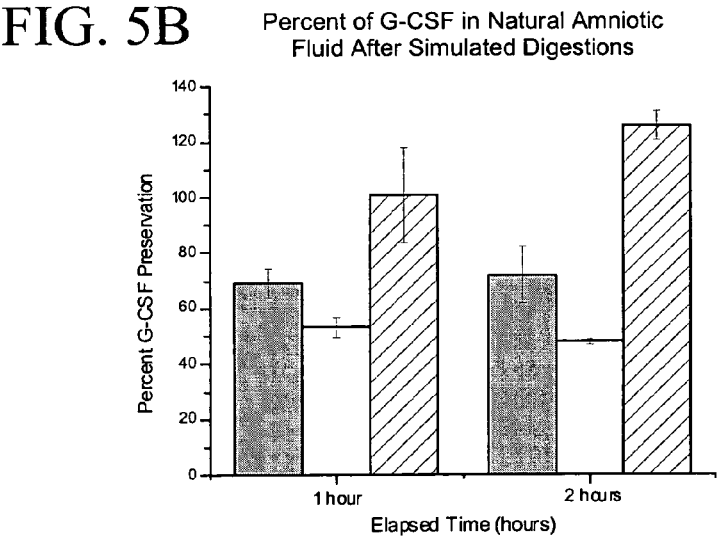
Figure 5C:
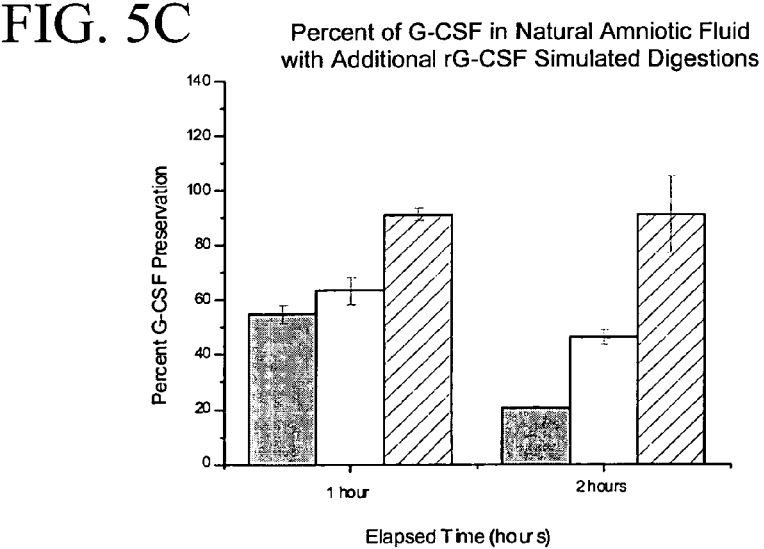

FIGS. 5A, 5B, and 5C show the percentage of filgrastim and natural G-CSF remaining after in vitro digestions. FIG. 5A shows the percentage of filgrastim in the composition of the subject invention at pH 3.2, 4.5, and 5.8. Greater than 50% of filgrastim remained after 1 hr and 2 hrs at pH 4.5 and 5.8. FIG. 5B shows the percentage of G-CSF in natural amniotic fluid after simulated digestions. Again, greater than 50% of G-CSF was measurable at 2 hrs at each pH. FIG. 5C shows the percentage of G-CSF measurable after simulated digestions of natural amniotic fluid to which additional filgrastim was added. G-CSF was significantly preserved at pH 5.89, and to a lesser degree at pH 3.2 and 4.5.

Figure 6A:
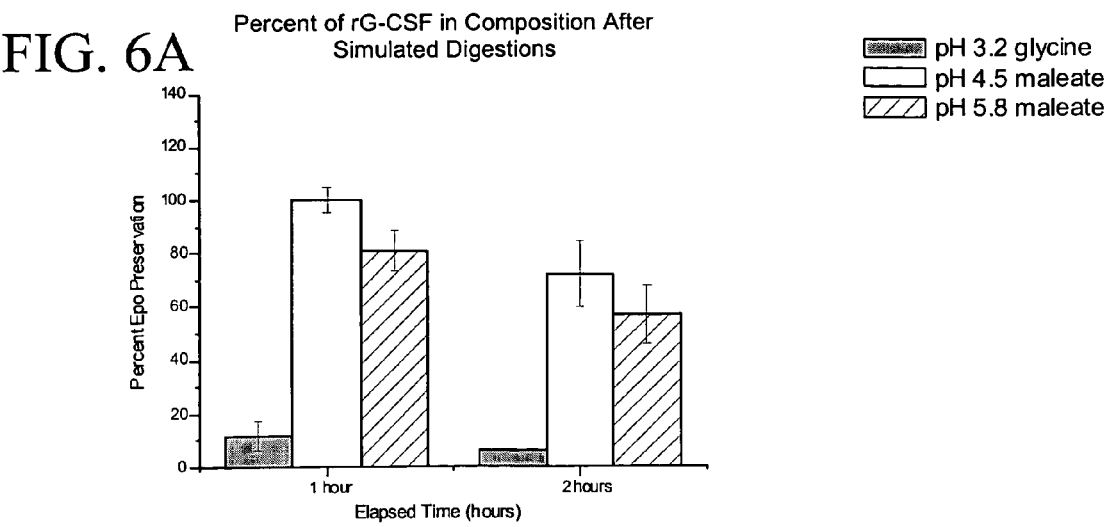
Figure 6B:
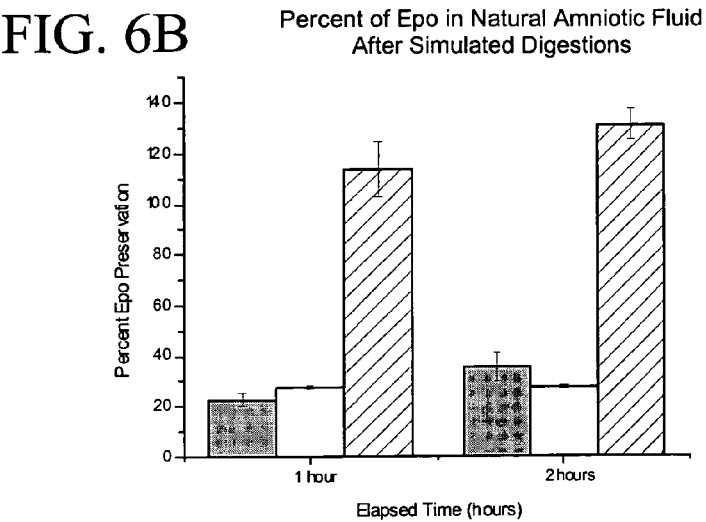
Figure 6C:
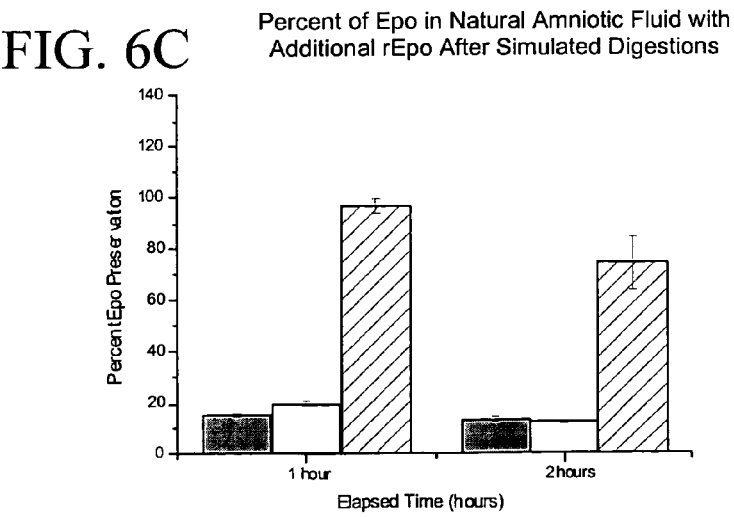

FIGS. 6A, 6B, and 6C show the percentage of epoetin alfa and Epo remaining after simulated in vitro digestions. FIG. 6A shows the percentage of epoetin alfa measurable in the composition of the subject invention at pH 3.2, 4.5, and 5.8. Greater than 50% of epoetin alfa remained after 1 hr and 2 hrs at pH 4.5 and 5.8. FIG. 6B shows the percentage of Epo measurable in natural amniotic fluid after simulated digestions. Epo was well protected from digestion at pH 5.8 at both 1 hr and 2 hrs, while only about 20% remained at pH 3.2 and 4.5. FIG. 6C shows the percentage of Epo measurable after simulated digestions of natural amniotic fluid to which additional epoetin alfa was added. Again, Epo was only significantly preserved at pH 5.8, and to a lesser degree at pH 3.2 and 4.5.

DETAILED DISCLOSURE OF THE INVENTION

The subject invention provides methods and compositions that promote or facilitate nutritional intake in low birth weight infants, preterm infants, and infants otherwise placed in the medical category of NPO (nothing per orum), receiving nothing by mouth. Specifically, the subject invention provides methods for reducing or preventing villous atrophy and feeding intolerance in infants by enterally administering granulocyte-colony stimulating factor (G-CSF), erythropoietin (Epo), or both G-CSF and Epo. In one aspect of the subject invention, recombinant G-CSF (rG-CSF, known generically as filgrastim) and/or recombinant Epo (rEpo, known generically as epoetin alfa) are administered. In a preferred embodiment of the subject invention, both G-CSF and Epo are administered. In a further preferred embodiment, G-CSF and Epo are administered to the neonate in concentrations comparable to those they would have ingested from amniotic fluid had they remained in utero.

The subject invention also provides compositions that comprise G-CSF and/or Epo that may be administered to infants in need thereof. In one embodiment, the composition of the subject invention comprises rG-CSF, rEpo, and one or more electrolyte additives. In a specific embodiment, the electrolyte additives are selected from the group consisting of sodium chloride, sodium acetate, and potassium chloride.

The compositions of the subject invention can be administered to an infant enterally. Preferably, the compositions are administered orogastrically and/or nasogastrically.

While the methods and compositions of the subject invention are particularly useful for facilitating nutritional intake in low birth weight and/or preterm infants, the methods and compositions of the subject invention are also directed to infants suffering from any condition in which they are placed in the medical category of NPO (nothing per orum). These infants often develop villous atrophy within 24 hours of not eating and may or may not be preterm and/or low birth weight.

The G-CSF and/or Epo used according to the subject invention are preferably recombinantly-derived, each being obtained as a product of the genetic transformation of a suitable host cell with a DNA sequence encoding G-CSF or Epo. More preferably, recombinant human G-CSF and recombinant human Epo are used.

The G-CSF and Epo for use in the subject invention include not only those polypeptides naturally produced in humans and other mammals, but also analogues of those polypeptides which possess the biological activity of natural or wild-type G-CSF and Epo.

In one embodiment, the composition of the subject invention includes one or more electrolyte additives, such as sodium acetate, sodium phosphate, potassium chloride, potassium phosphate, calcium gluconate, and magnesium sulfate. In a preferred embodiment, the electrolyte additive is selected from the group consisting of sodium chloride, sodium acetate, and potassium chloride.

In a further embodiment, the compositions of the subject invention include various other components known to be found within amniotic fluid at the various gestational terms, such as albumin, bilirubin, chloride, creatinine, estriol, and lecithin/sphingomyelin.

In a specific embodiment, the composition of the subject invention comprises about 225 ng/mL (0.12 mL of G-CSF 300 mcg/mL in 160 mL) of G-CSF, about 4.375 u/mL (0.35 mL of Epo 2000 u/mL in 160 mL) of Epo, about 115 mEq/L of NaCl, about 17 mEq/L of Na acetate, about 4 mEq/L of KCl, and about 0.05% of albumin. A variety of fluids can be used as diluents in the compositions of the subject invention, such as sterile water.

In one embodiment, the composition of the subject invention comprises about 0.001% albumin to about 1% albumin. In another embodiment, the composition of the subject invention comprises about 0.01% albumin to about 0.1% albumin. In a further embodiment, the composition of the subject invention comprises about 0.03% albumin to about 0.07% albumin. In a preferred embodiment, the composition of the subject invention comprises about 0.05% albumin.

In another embodiment, the composition of the subject invention comprises about 10 mEq/L of NaCl to about 500 mEq/L of NaCl. In a further embodiment, the composition comprises about 50 mEq/L of NaCl to about 250 mEq/L of NaCl. In another embodiment, the composition of the subject invention comprises about 1 mEq/L Na acetate to about 100 mEq/L Na acetate. In a further embodiment, the composition comprises about 5 mEq/L Na acetate to about 50 mEq/L Na acetate. In another embodiment, the composition of the subject invention comprises about 0.1 mEq/L KCl to about 50 mEq/L KCl. In a further embodiment, the composition comprises about 2 mEq/L KCl to about 10 mEq/L KCl.

The compositions of the subject invention can include further nutrients, such as amino acids, carbohydrates, lipids, vitamins, and minerals. Appropriate vitamins include, for example, vitamin A (retinol), vitamin $B^1$ (thiamine), vitamin $B^2$ (riboflavin), vitamin $B^6$ (pyridoxine), vitamin $B^{12}$ (cyanocobalamin), vitamin C (ascorbic acid), vitamin D (ergo Calciferol), vitamin E, biotin, folic acid, niacinamide, and pantothenic acid. The compositions of the subject invention can also include various trace elements, such as copper, manganese, and chromium.

The compositions of the subject invention can also include one or more surfactants. Surfactants useful in the practice of the subject invention include, but are not limited to, anionic surfactants, cationic surfactants, and nonionic surfactants. Examples of anionic surfactants include, but are not limited to, sodium lauryl sulfate, dioctyl sodium sulfosuccinate, and dioctyl sodium sulfate. Examples of cationic surfactants include, but are not limited to, benzalkonium chloride and benzethonium chloride. Examples of nonionic surfactants include, but are not limited to, lauromacrogol 400; polyoxyl 40 stearate; polyoxyethylene hydrogenated castor oil 10, 50, and 60; glycerol monostearate; polysorbate 40, 60, 65, and 80; sucrose fatty acid ester; methylcellulose; and carboxymethyl cellulose.

The compositions of the subject invention can also include one or more excipients. Excipients useful in the practice of the subject invention include, but are not limited to, starches, sugars, inorganic substances, organic acids, celluloses, synthetic and semisynthetic polymers, amino acids. Examples of starches include corn starch, wheat starch, potato starch, and the like. Examples of sugars include lactose, glucose, saccharose, fructose, D-sorbitol, D-mannitol, inositol, sucrose, and the like. Examples of inorganic substances include magnesium stearate, calcium phosphate, calcium hydrogen carbonate, magnesium carbonate, sodium chloride, calcium sulfate, and so forth. Examples of organic acids include succinic acid, tartaric acid, citric acid, fumaric acid, maleic acid, malonic acid, glutaric acid, adipic acid, malic acid, gluconic acid, glucuronic acid, and the like. Examples of celluloses include microcrystalline cellulose, methylcellulose, ethylcellulose, hydroxyethyl cellulose, hydroxypropyl cellulose, carboxypropyl cellulose, carboxymethyl cellulose sodium, and so forth. Examples of synthetic and semi-synthetic polymers include polyvinyl alcohol, carboxyvinyl polymer, polyethylene glycol (PEG), polyvinylpyrrolidone, sodium polyacrylate, and the like. Examples of amino acids include L-arginine, D- or L-methionine, L-phenylalanine, L-glutamic acid, and so forth.

According to the preferred methods of the subject invention, a G-CSF and Epo containing composition is administered enterally. Preferably, the composition is administered either orogastrically or nasogastrically. The composition can be administered to the gastrointestinal tract by a variety of techniques and apparatus known to those skilled in the art. Preferably, the compositions of the subject invention are administered by gravity through syringes attached to feeding tubes (e.g., polyvinyl chloride feeding tubes), as is the practice in neonatal intensive care units (NICU) of hospitals.

In a preferred embodiment, the compositions of the subject invention are used with infants having a birth weight of less than about 2000 grams. The compositions of the subject invention can also be administered to very low birth weight infants (less than about 1500 grams) and extremely low birth weight infants (less than about 1000 grams). The compositions of the subject invention are particularly useful to infants having a birth weight from about 750 to 1250 grams.

Preterm infants are typically those having completed less than about 37 weeks gestation. The compositions of the subject invention can also be administered to those infants considered to be on the edge of viability, based on gestation (having completed about 23–24 weeks gestation).

While the methods and compositions of the subject invention are particularly useful for facilitating nutritional intake in low birth weight and/or preterm infants, the methods and compositions of the subject invention are also directed to infants suffering from a condition in which they are placed in the medical category of NPO (nothing per orum), receiving nothing by mouth. Therefore, in a further aspect of the subject invention, the compositions of the subject invention can be enterally administered to infants suffering from a gut catastrophe, such as necrotizing enterocolitis, and thus rendered NPO. These infants may or may not be preterm and/or low birth weight. In addition, the compositions of the subject invention can be administered to infants suffering from congenital anomalies of the gastrointestinal tract which render the infant NPO. Examples of such congenital anomalies include tracheoesophageal fistulas, valocoels, and congenital diaphragmatic hernias. Infants suffering from such gastrointestinal abnormalities may or may not be preterm and/or low birth weight. Therefore, the methods of the subject invention include the enteral administration of G-CSF and Epo to any neonate rendered NPO, as these infants are at risk for villous atrophy, feeding intolerance, and necrotizing enterocolitis.

Preferably, the composition of the subject invention is administered in volumes less than the volume of natural amniotic fluid that the infant would have received in utero (about 200 mL per day). In one embodiment, the volume of the composition administered is from about 2 mL to about 100 mL per day. In a further embodiment, the volume of the composition administered is from about 5 mL to about 50 mL per day. In another embodiment, the volume of the composition administered is from about 10 mL to about 30 mL per day. In another embodiment, the composition of the subject invention is administered in the amount of about 20 mL per day.

The compositions of the subject invention are preferably administered to the infant such that the G-CSF and/or Epo concentrations approximate what the infant would have received in the form of natural amniotic fluid in utero (in the case of preterm infants). In one embodiment, about 1,000 ng to about 10,000 ng of G-CSF are administered and/or about 10 units to about 200 units of Epo are administered per day. In another embodiment, about 2,500 to about 7,500 ng of G-CSF and/or about 50 units to about 150 units of Epo are administered per day. In a further embodiment, about 3,500 ng to about 5,500 ng of G-CSF and/or about 75 units to about 100 units of Epo are administered per day. In a specific embodiment, about 4,500 ng of G-CSF and/or about 87.5 units of Epo are administered in about 20 mL of solution per day. In the case of full term infants otherwise in need of G-CSF and/or Epo, the compositions of the subject invention can be administered in the same or similar volumes and concentrations as in the case of preterm infants. In a further aspect of the subject invention, the composition can be administered in several doses over a period of time, e.g., in equal doses every three hours (over eight time periods). In a specific embodiment, about 2.5 mL of the composition are administered in about three hour intervals so that about 4,500 ng of G-CSF and/or about 87.5 units of Epo are administered per day. In a further aspect of the subject invention, the composition can be enterally administered to a neonate after a period of NPO (e.g., three days), as a primer for other enterally delivered nutritional substances.

In a further related aspect of the subject invention, the composition of the subject invention can be administered in a variety of dosage forms. While it is preferred that the consistency of the composition of the subject invention approximates that of natural amniotic fluid, other forms and consistencies could be used by those skilled in the art having the benefit of the current disclosure. For example, the compositions of the subject invention can be formulated and administered in an aqueous fluid-like form or as a slow-release gel.

Experiments were conducted to determine the stability of recombinant granulocyte colony-stimulating factor (rG-CSF, filgrastim) and recombinant erythropoietin (rEPO, epoetin alfa) in a solution designed for enteral administration in the neonatal intensive care unit (NICU), as described in Examples 1 and 2. The results show that filgrastim and epoetin alfa in the composition of the subject invention are stable when frozen for three weeks or refrigerated for 24 hours, and that their concentrations are minimally reduced if preceded by adequate priming of the polyvinyl chloride feeding tube. Therefore, the composition of the subject invention can be prepared well in advance and frozen at, for example, −80° C. until used. Prior to patient administration, the aliquot can be thawed and refrigerated at, for example, 4° C. The aliquot can then be warmed to room temperature prior to administration of the composition to the neonate.

The pharmacologic availability of filgrastim and epoetin alfa in the composition of the subject invention, using the routes of administration typically utilized in the art, was also determined. It was previously unknown how administering the fluid by gravity through syringes attached to polyvinyl chloride feeding tubes, as is the practice in the neonatal intensive care unit (NICU), would affect the pharmacologic availability of filgrastim and epoetin alfa (Ohls et al. [1996] *Ann Pharmacother* 30:466–8). Therefore, a series of in vitro experiments were designed to answer this question, as described in Examples 1 and 2, and FIGS. 1–4. Filgrastim concentrations did not vary significantly before, during, or after priming of the feeding tube, whereas epoetin alfa concentrations decreased significantly unless the feeding tube was primed with 10 mL of solution. Thus, filgrastim and epoetin alfa were stable in the composition of the subject invention.

In addition, to determine the stability of recombinant G-CSF and Epo within the neonatal stomach, simulated digestion experiments were conducted at pH concentrations of 3.2, 4.5, and 5.8. As described in Example 3 and FIGS. 5A–5C and 6A–6C, G-CSF and Epo in natural amniotic fluid, and filgrastim and epoetin alfa in the composition of the subject invention, remain relatively non-degraded under digestive conditions, except at the lowest pH conditions tested.

All patents, patent applications, provisional applications, and publications referred to or cited herein are incorporated by reference in their entirety to the extent they are not inconsistent with the explicit teachings of this specification.

Materials and Methods

Preparation of Amniotic Fluid-like Solution for Stability Studies. A solution that mimicked the electrolyte content of human amniotic fluid (Calhoun et al. [1998] *J Soc Gynecol Invest* 5:176 A; Clapp et al. [1995] *Am J Obstet Gynecol* 172:1445–51; Sinha [1970] *J Obstet Gynaecol* 77:211–4; Lind et al. [1971] *J Obstet Gynaecol* 78:505–12; Benzie et al. [1974] (A) *Am J Obstet Gynecol* 78:505–12; Emery [1970] *Lancet* 760:1307–8) was prepared in a polyvinyl chloride intravenous infusion bag (VIAFLEX, Baxter Healthcare Corp., Deerfield, Ill.). The fluid contained 115 mEq/L of NaCl 0.9%, 17 mEq/L of sodium acetate, and 4 mEq/L of potassium chloride. Recombinant human G-CSF, known generically as filgrastim (NEUPOGEN, Amgen, Inc., Thousand Oaks, Calif.), and recombinant human Epo, known generically as epoetin alfa (EPOGEN, Amgen Inc.), were obtained from the hospital pharmacy at concentrations of 300 μg/mL (filgrastim) and 2000 U/mL (epoetin alfa). Amounts were added to the electrolyte solution under sterile conditions to achieve a final calculated concentration of 225 ng/mL (filgrastim) and 4400 mU/mL (epoetin alfa).

The concentrations of filgrastim and epoetin alfa in the amniotic fluid-like solution were 10 times the normal concentration of each cytokine in amniotic fluid (Calhoun et al. [1998] supra; Clapp et al. [1995] supra; Sinha [1970] supra; Lind et al. [1971] supra; Benzie et al. [1974] (B) *Am J Obstet Gynecol* 119:798–810; Emery [1970] *Lancet* 760:1307–8). These concentrations were selected since only one-tenth the volume normally swallowed in utero would be given to the neonate (i.e., 20 mL/kg/d rather than 200 mL/kg/d). Human serum albumin 5% (Baxter Healthcare Corp., Hyland Division, Glendale, Calif.) was added to the infusion bag prior to the addition of the cytokines (final concentration of albumin 0.05%). Aliquots of the amniotic fluid-like solution were either tested for stability immediately after preparation (as described in Examples 1 and 2), held at room temperature for specified time periods (6 h, 12 h, 18 h, or 24 h), or stored at −80° C. until analysis.

Preparation of Amniotic Fluid-like Solution for Simulated Digestion Studies. The solution (N=5 preparations) was prepared identically to the solution prepared for the stability studies. The concentration of filgrastim and epoetin alfa were verified in each new batch of solution, and the pH of the solution was also measured. Aliquots of the solution were also tested for stability, as described in Examples 1 and 2.

Collection of Natural Amniotic Fluid. Amniotic fluid (N=15) was collected by transabdominal amniocenteses performed for medical indications. Samples were immediately centrifuged at 1500×g for 10 minutes, pooled, and frozen at −80° C. until analysis. The pH of the pooled amniotic fluid was tested prior to analysis.

Collection of Gastric Secretions. Gastric juices were collected from premature infants (<34 weeks gestation) who had an existing indwelling orogastric or nasogastric catheter, were less than three days of age, and were not receiving any oral feedings. Secretions were pooled and frozen at −80° C. At the time of assay, they were cleared of particulate material by centrifugation at 14,000×g for 10 minutes. The pH of the pooled gastric secretions was determined prior to their use in the simulated digestions, which are described in Example 3.

G-CSF Enzyme-Linked Immunosorbent Assay. G-CSF was quantified by enzyme-linked immunosorbent assay (ELISA; QUANTIKINE Human G-CSF Immunoassay, R&D Systems, Minneapolis, Minn.; lower limit of sensitivity 20 pg/mL). The assay uses the quantitative sandwich immunoassay technique, using a monoclonal antibody specific for G-CSF. G-CSF concentrations between 20 and 2500 pg/mL can be measured. There is no measurable cross-reactivity with other cytokines, and the assay recognizes both natural and recombinant G-CSF. The assay uses 100 μl of sample.

Epo Enzyme-Linked Immunosorbent Assay. Epo was quantified by ELISA (QUANTIKINE Human Epo Immunoassay, R&DF Systems; lower limit of sensitivity 0.6 U/mL). The assay uses a monoclonal antibody and polyclonal antibody conjugate in a sandwich ELISA format, and measures epoetin concentrations between 0.6 and 200 mU/mL. The assay has no measurable cross-reactivity with other cytokines, and recognizes both natural and recombinant Epo. The assay uses 100 µl of sample.

Data Analysis. Concentrations of filgrastim and epoetin alfa are expressed as means±standard error of the mean. For statistical analysis, a Student's t-test was used (Primer of Biostatistics software, WINDOWS version 4.02, McGraw-Hill, New York, 1996). An α level <0.05 was considered significant. In the digestion studies, G-CSF and Epo concentrations remaining in reaction mixtures at 1 and 2 hours were compared with baseline concentrations using multiple paired t tests.

Following are examples which illustrate procedures for practicing the invention. These examples should not be construed as limiting. All percentages are by weight and all solvent mixture proportions are by volume unless otherwise noted.

EXAMPLE 1

Stability of Recombinant Granulocyte-Colony Stimulating Factor

For the experiments described in Examples 1 and 2, filgrastim and epoetin alfa were added to a solution with NaCl 0.9%, sodium acetate, potassium chloride, and human albumin in concentrations designed to mimic human amniotic fluid. Additionally, the composition was dripped through polyvinyl chloride feeding tubes to simulate feedings, and aliquots were collected before, during, and after priming of the tube. Other aliquots were either frozen immediately, stored at room temperature, or refrigerated for 0, 6, 12, 18, and 24 hours. Filgrastim and epoetin alfa concentrations in the various aliquots were then compared with the concentrations in the original solution.

Figure 1:
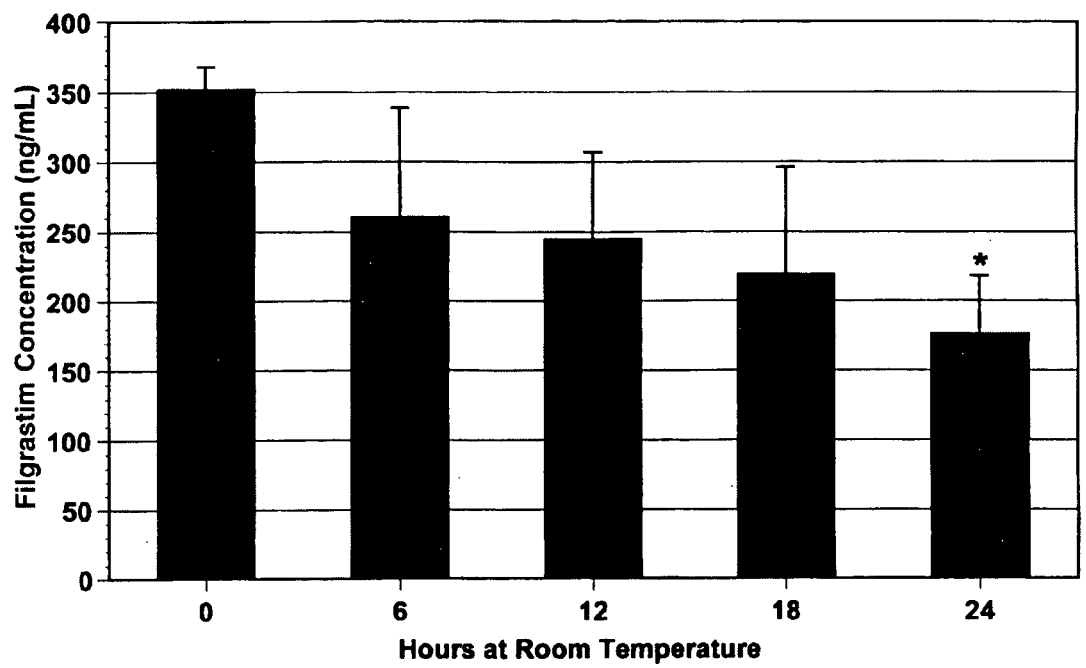
FIG. 1 shows filgrastim concentrations (mean+/–SEM) in specific compositions of the subject invention. The concentration of filgrastim was measured in aliquots of solution stored at room temperature for up to 24 hours. At specific intervals (6, 12, 18, or 24 hours) aliquots were frozen at −80° C. until analysis. Each time point represents the average concentration of five solutions (p=0.001).
Figure 2:
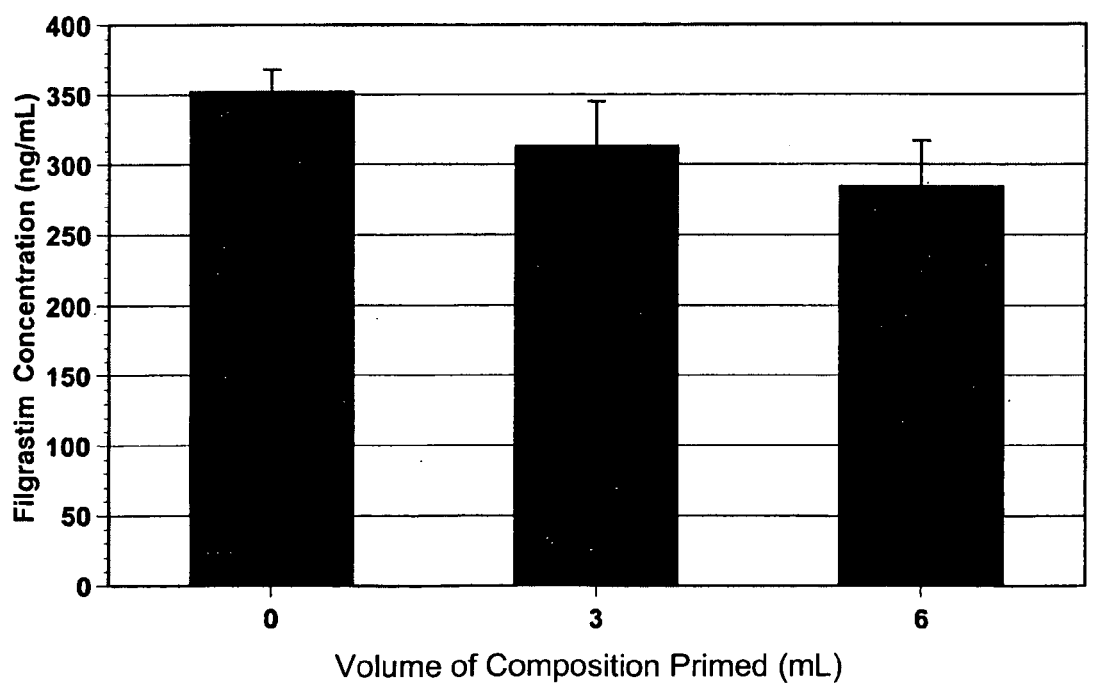
FIG. 2 shows filgrastim concentrations (mean+/–SEM) before, during, and after priming of the feeding tube.

The measured concentration of filgrastim in the composition of the subject invention was consistently higher than the calculated value (measured, 352±16 vs. calculated, 225 ng/mL; n=5). The stability of filgrastim in the composition of the subject invention was not significantly affected by refrigeration or freezing. No significant difference in concentration was noted between freshly prepared solutions and refrigerated solutions that were evaluated at six-hour intervals over a 24-hour period (352±16 vs. 332±20 ng/mL, respectively; n=5 per group). Similarly, no difference in filgrastim concentration was noted between freshly prepared solutions and aliquots that had been frozen for up to three weeks (352±16 vs. 378±20 ng/mL, respectively). However, when the solution was stored at room temperature, a continual decrease in filgrastim concentration was observed over a 24-hour period (FIG. 1). At 24 hours, the concentration of filgrastim was significantly less than at time zero (p=0.01). When the recovery of filgrastim was evaluated after passage through a polyvinyl chloride feeding tube, no significant difference in concentration was seen compared with the concentration of filgrastim in solutions not passed through a feeding tube (p=0.54 for initial prime and p=0.12 for second prime compared with stock solution). The percent recovery was 89%±20%. After the initial priming of the feeding tube, the concentration of filgrastim did not differ from that obtained during the prime (313±32 vs. 284±32 ng/mL, respectively; FIG. 2).

EXAMPLE 2

Stability of Recombinant Erythropoietin

The measured concentration of epoetin alfa in the composition of the subject invention was consistently lower than the calculated value (measured, 2860±185 vs. calculated, 4400 mU/mL; n=5). It was stable at room temperature for up to 24 hours, with no difference between freshly prepared solutions and room temperature-exposed solutions (2860±185 vs. 2695±134 mU/mL at time zero and at 24 hours, respectively; n=5 per group; FIG. 3). The solution was stable when frozen, with no further decrease in epoetin alfa concentration for up to three weeks. After freezing for one month, however, a slight but significant decrease in epoetin alfa concentration was noted (2860±185 vs. 2353±59 mU/mL, respectively; n=5; p<0.05). There was also a decrease in epoetin alfa concentrations after passing the solution through a polyvinyl chloride feeding tube (FIG. 4). The initial epoetin alfa concentration was 2742±152 mU/mL (n=12). After a 3-mL prime through the feeding tube, the concentration was 2189±166 mU/mL (n=5), and after a second 3 mL was passed through the catheter, the concentration was 2060±378 mU/mL (n=5). After priming with 10 mL of epoetin alfa-containing solution, there were no further decreases in measured epoetin alfa concentration.

The information in these stability experiments is important when considering the enteral administration of filgrastim and epoetin alfa to neonates. The results show that filgrastim and epoetin alfa in the composition of the subject invention are stable when frozen for three weeks or refrigerated for 24 hours, and that their concentrations are minimally reduced if preceded by adequate priming of the polyvinyl chloride feeding tube.

EXAMPLE 3

Simulated Digestion

The susceptibility of filgrastim and epoetin alfa to degradation within compositions of the subject invention and within pooled human amniotic fluid was evaluated using neonatal gastric secretions as an in vitro simulation of neonatal digestion (Kling et al. [1998] *Pediatr Res* 43:216–21; Calhoun et al. [2001] *Obstet Gynecol* 97:229–34). Preterm gastric secretions were used exclusively. Simulations were run for 0 (baseline degradation), 1 hr, and 2 hrs. These intervals were selected because, after human milk feedings, maximal gastric acid proteolytic activity occurs at 1 hr, and although continuous, stomach emptying generally occurs between 1 hr and 2 hrs. To approximate neonatal gastrointestinal luminal conditions without interfering with proteolytic activity, two incubation buffers were used in standard reaction mixtures (Kling et al. [1998] supra). The buffers consisted of: 1) 0.1 M glycine at pH 3.2 to simulate preprandial gastric conditions, and 2) 0.1 M maleate at pH 5.8 to simulate postprandial gastric conditions. A third buffer consisting of 0.1 M maleate at pH 4.5 was used to assess the independent effect of pH on digestion. The standard reaction mixture included one of the three buffers, neonatal gastric juices, and the substrate (the composition of the subject invention or pooled natural amniotic fluid).

To ensure that endogenous enzymes were active for each simulation, 50 μL of each of the three pH buffers was preincubated for 15 min. at 37° C. with 50 μL aliquots of pooled, thawed, and cleared, neonatal gastric secretions. To start the reaction, a 50 μL aliquot of substrate was added and incubated at 37° C. (150 μL total volume). Reaction mixtures were evaluated at each pH buffer condition, on all substrates, for baseline, 1 hr and 2 hrs at 37° C. At the end of the incubations, 5 μL of 1 M Tris buffer, pH 8, was added to stop the reaction. Samples were then frozen at −80° C. until assay.

The pH of the pooled natural amniotic fluid was 8.0. The concentration of G-CSF in this amniotic fluid prior to digestion was 13,475 pg/mL, and the concentration of Epo was 192 mU/mL. The pH of the composition of the subject invention was 6.0. The concentrations of filgrastim and epoetin alfa in the composition of the subject invention prior to digestion were similar to the calculated concentrations. The pH of the pooled neonatal gastric secretions was 3.0.

The concentrations of G-CSF remaining at 1 hr and 2 hrs were compared to the concentration at time zero, as shown in FIGS. 5A, 5B, and 5C. G-CSF was measured in the natural amniotic fluid, the composition of the subject invention, and also in natural amniotic fluid to which filgrastim and epoetin alfa had been "spiked." Significant G-CSF (at least 50%) remained in each of the solutions at the end of two hours at pH 4.5 and pH 5.8. At pH 3.2, greater than 50% of G-CSF was measurable in the natural amniotic fluid, while significantly less was noted in the synthetic amniotic fluid or in natural amniotic fluid to which filgrastim had been added.

The concentrations of Epo remaining at 1 hr and 2 hrs are compared to the concentration at time zero, as shown in FIGS. 6A, 6B, and 6C. More than 50% of Epo was measurable in each of the solutions at pH 5.8 at the end of the two hours. At pH 4.5, significant quantities of epoetin alfa were only measurable in the composition of the subject invention; and at pH 3.2, none of the solutions contained substantial quantities of Epo.

Under these in vitro conditions that simulate preprandial and postprandial conditions of neonates, endogenous G-CSF and Epo in natural amniotic fluid, and filgrastim and epoetin alfa in a composition of the subject invention were relatively resistant to degradation, except at the lowest pH conditions tested. Therefore, the amount of degradation was influenced by the pH of the reaction mixtures as demonstrated by the increased degradation at pH 3.2, as compared with both pH 4.5 and 5.8. Activation of specific proteases is pH dependent. Since the major determinants of proteolysis are proteases and pH (Britton, J. [1989] *J Pediatr Gastroenterol and Nutr,* 9(2):144–62), this pH related effect is not unusual.

The pH of the gastric secretions obtained from the neonates in this study was similar to published reports. Investigators have noted that on the first day of life, the pH of neonatal gastric secretions at 24 to 29 weeks gestation averaged about 3.0 (Kelly et al. [1994] *Early Hum Dev* 35:215–20), but this increased markedly following feeding. Beyond the newborn period, there is absence of agreement concerning the pattern of development of gastric acidity: some reports suggest constancy of pH during the first few weeks postnatally (Ames, M. [1966] *Am J Dis Child* 100: 252–6), while others suggest that as the postnatal age increases, the gastric pH decreases (Cothran et al. [1997] *J Perinatol* 17:383–8). In neonates receiving ranitidine, the gastric pH averages about 5.6. The pH of amniotic fluid ranges from 6.96–7.20 with an average value of 7.04 (Bonsnes, R. [1966] *Clin Obstet Gynecol* 9:440–8). The pH of the pooled natural amniotic fluid in this study and of the synthetic amniotic fluid were similar to this range.

These digestion experiments confirm that 1) G-CSF and Epo in natural amniotic fluid, and filgrastim and epoetin alfa in compositions of the subject invention are relatively protected from gastrointestinal degradation, and 2) even at pH 3, more than 20% of filgrastim and >10% of epoetin alfa are still recognized by the ELISA after one hour of digestion. Thus, a significant fraction of filgrastim and epoetin alfa in this formulation are biologically available after enteral administration to preterm neonates.

It should be understood that the examples and embodiments described herein are for illustrative purposes only and that various modifications or changes in light thereof will be suggested to persons skilled in the art and are to be included within the spirit and purview of this application.

What is claimed is:

1. A method for reducing feeding intolerance in an infant suffering from a condition of the gastrointestinal tract that causes the infant to be feeding intolerant, comprising enterally administering granulocyte-colony stimulating factor and erythropoietin to the infant, wherein the granulocyte-colony stimulating factor and erythropoietin are administered to the infant together within the same formulated composition or within separate formulated compositions, and wherein said administering reduces feeding intolerance in the infant.

2. The method according to claim 1, wherein the granulocyte-colony stimulating factor and erythropoietin are administered to the infant within the same composition.

3. The method according to claim 1, wherein the granulocyte-colony stimulating factor is recombinantly derived.

4. The method according to claim 1, wherein the erythropoietin is recombinantly derived.

5. The method according to claim 1, wherein the granulocyte-colony stimulating factor is mammalian granulocyte-colony stimulating factor.

6. The method according to claim 1, wherein the erythropoietin is mammalian erythropoietin.

7. The method according to claim 1, wherein said enteral administration is orogastric, nasogastric, or both orogastric and nasogastric.

8. The method according to claim 1, wherein the granulocyte-colony stimulating factor and erythropoietin are administered to the infant through a syringe attached to a feeding tube.

9. The method according to claim 1, wherein the method further comprises administering one or more electrolytes to the infant.

10. The method according to claim 1, wherein the method further comprises administering one or more electrolytes to the infant selected from the group consisting of sodium acetate, sodium phosphate, potassium chloride, potassium phosphate, calcium gluconate, and magnesium sulfate.

11. The method according to claim 1, wherein the method further comprises administering one or more electrolytes to the infant selected from the group consisting of sodium chloride, sodium acetate, and potassium chloride.

12. The method according to claim 1, wherein the method further comprises administering a component of amniotic fluid selected from the group consisting of albumin, bilirubin, chloride, creatinine, estriol, lecithin, and sphingomyelin.

13. The method according to claim 1, wherein the method further comprises administering albumin and one or more electrolytes selected from the group consisting of sodium chloride, sodium acetate, and potassium chloride.

14. The method according to claim 13, wherein the granulocyte-colony stimulating factor and erythropoietin are administered to the infant within the same composition, and wherein the albumin and one or more electrolytes are administered to the infant in the same composition as the granulocyte-colony stimulating factor and erythropoietin.

15. The method according to claim 1, wherein said method further comprises administering albumin, sodium chloride, sodium acetate, and potassium chloride.

16. The method according to claim 1, wherein about 1,000 ng to about 10,000 ng of granulocyte-colony stimulating factor are administered to the infant per day.

17. The method according to claim 1, wherein about 2,500 ng to about 7,500 ng of granulocyte-colony stimulating factor are administered to the infant per day.

18. The method according to claim 1, wherein about 3,500 ng to about 5,500 ng of granulocyte-colony stimulating factor are administered to the infant per day.

19. The method according to claim 1, wherein the granulocyte-colony stimulating factor is administered to the infant at a concentration of about 225 ng/mL.

20. The method according to claim 1, wherein about 10 units to about 200 units of erythropoietin are administered to the infant per day.

21. The method according to claim 1, wherein about 50 units to about 150 units of erythropoietin are administered to the infant per day.

22. The method according to claim 1, wherein about 75 units to about 100 units of erythropoietin are administered to the infant per day.

23. The method according to claim 1, wherein the erythropoietin is administered to the infant at a concentration of about 4.375 units/mL.

24. The method according to claim 1, wherein the granulocyte-colony stimulating factor and erythropoietin are administered within the same composition and the composition is administered to the infant in a volume of less than about 200 mL per day.

25. The method according to claim 1, wherein the granulocyte-colony stimulating factor and erythropoietin are administered within the same composition and the composition is administered to the infant in a volume of about 2 mL to about 100 mL per day.

26. The method according to claim 1, wherein the granulocyte-colony stimulating factor and erythropoietin are administered within the same composition and the composition is administered to the infant in a volume of about 5 mL to about 50 mL per day.

27. The method according to claim 1, wherein the granulocyte-colony stimulating factor and erythropoietin are administered within the same composition and the composition is administered to the infant in a volume of about 10 mL to about 30 mL per day.

28. The method according to claim 1, wherein the granulocyte-colony stimulating factor and erythropoietin are administered within the same composition and the composition is administered to the infant in a volume of about 20 mL per day.

29. The method according to claim 1, wherein the same or separate compositions are in fluid form.

30. The method according to claim 1, wherein the same or separate compositions are each a slow-release gel.

31. The method according to claim 1, wherein the infant is human.

32. The method according to claim 1, wherein the infant is a preterm infant.

33. The method according to claim 1, wherein the infant is of low birth weight.

34. The method according to claim 1, wherein the infant is preterm and of low birth weight.

35. The method according to claim 1, wherein the infant is human and has a birth weight of less than about 2000 grams.

36. The method of claim 1, wherein the infant is human and has a birth weight of less than about 1500 grams.

37. The method of claim 1, wherein the infant is human and has a birth weight of less than about 1000 grams.

38. The method of claim 1, wherein the infant is human and has a birth weight from about 750 grams to about 1250 grams.

39. The method of claim 1, wherein the infant is human and has completed less than about 37 weeks of gestation.

40. The method of claim 1, wherein the infant is human and has completed from about 23 weeks to about 24 weeks of gestation.

41. The method of claim 1, wherein the infant is human and the condition of the gastrointestinal tract places the infant in the medical category of nothing per orum (NPO).

42. The method of claim 41, wherein the condition is necrotizing enterocolitis (NEC).

43. The method of claim 41, wherein the condition is a congenital anomaly of the gastrointestinal tract.

44. The method of claim 41, wherein the condition is a congenital anomaly selected from the group consisting of tracheoesophageal fistula and congenital diaphragmatic hernia.

45. The method of claim 1, wherein the infant is a full term infant.

46. A method for reducing villous atrophy in a human infant, comprising enterally administering granulocyte-colony stimulating factor and erythropoietin to the infant, wherein the granulocyte-colony stimulating factor and erythropoietin are administered to the infant within the same formulated composition or within separate formulated compositions, and wherein said administering reduces villous atrophy in the infant.

47. The method of claim 46, wherein the infant is a pre-term infant.

48. The method of claim 46, wherein the infant is of low birth weight.

* * * * *

UNITED STATES PATENT AND TRADEMARK OFFICE
CERTIFICATE OF CORRECTION

PATENT NO. : 6,956,023 B1
DATED : October 18, 2005
INVENTOR(S) : Darlene Vasbinder Calhoun and Robert Dennis Christensen It is certified that error appears in the above-identified patent and that said Letters Patent is hereby corrected as shown below:

Column 1,
Line 39, "*Sci* 54:87" should read -- *Sci* 54:85-87 --.

Column 2,
Line 1, "*et al.* [1 *J Surg Res*" should read -- *et al.* [1986] *J Surg Res* --.

Signed and Sealed this

Seventh Day of February, 2006

JON W. DUDAS
*Director of the United States Patent and Trademark Office*